(12) United States Patent
Chen et al.

(10) Patent No.: US 8,722,364 B2
(45) Date of Patent: May 13, 2014

(54) METHOD FOR INCREASING MICROBIAL CATALASE PRODUCTION

(75) Inventors: Jian Chen, Wuxi (CN); Guocheng Du, Wuxi (CN); Jianghua Li, Wuxi (CN); Long Liu, Wuxi (CN); Zhuolin Feng, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 349 days.

(21) Appl. No.: 13/228,572

(22) Filed: Sep. 9, 2011

(65) Prior Publication Data
US 2013/0065292 A1 Mar. 14, 2013

(51) Int. Cl.
*C12P 21/04* (2006.01)

(52) U.S. Cl.
USPC ........................................ 435/71.2; 435/71.1

(58) Field of Classification Search
None
See application file for complete search history.

(56) References Cited

FOREIGN PATENT DOCUMENTS

CN ZL 200610040898.0 * 7/2006 ............... C12N 1/20

OTHER PUBLICATIONS

"Catalase" Worthington Enzyme Manual, Worthington Biochemical Corporation, 3 pages viewed Oct. 20, 2013.*
Chelikani et al. "Diversity of structures and properties among catalases" Cell. Mol. Life Sci. 61 (2004) 192-208.*

* cited by examiner

*Primary Examiner* — Thane Underdahl
(74) *Attorney, Agent, or Firm* — Lili Chen

(57) ABSTRACT

Disclosed are methods for increasing microbial catalase production. 1-10 g/L sodium hexametaphosphate was added to the culture medium between 30-40 hours of fermentation to inhibit proteinase activity and increase the production of catalase. This simple modification of fermentation procedure can result in up to 45% increase of the production of catalase.

6 Claims, No Drawings

METHOD FOR INCREASING MICROBIAL CATALASE PRODUCTION

BACKGROUND OF THE INVENTION

1. Field of the Invention

The present invention is in the field of fermentation technologies. It particularly relates to a method for increasing microbial catalase production by addition of sodium hexametaphosphate.

2. Description of the Related Art

Catalase (referred to as CAT) is an enzyme that catalyzes the decomposition of $H_2O_2$ to $H_2O$ and $O_2$. It acts as a regulator of $H_2O_2$ levels in cells and protects organisms from the damage of Reactive Oxygen Species. Catalases are widely utilized in areas such as food sterilization, clinical analysis, and disease diagnosis as well as in textile, paper, and pulp industries. Catalase is used for removal of hydrogen peroxide in the textile pretreatment as a substitute for high-temperature water washing and using chemical reducing agents. Most catalases consist of four identical subunits, with a total molecular weight of around 240 kDa. In recent years, with the widespread application of catalases in textile, paper, and pulp industries, the market demand for catalases has significantly increased.

Development of novel technologies for increasing the yield of catalase is important for industrial production and application of this enzyme, which can reduce the production cost and achieve higher economic efficiency so as to meet the increasing industrial demand.

Sodium hexametaphosphate is a low cost inorganic protective agent that inhibits activity of proteinases and protects catalases from being digested by proteinases. It has not been reported to increase calatase production by addition of sodium hexametaphosphate.

DETAILED DESCRIPTION

The objective of this invention is to provide a method for increasing microbial catalase production.

The present invention provides a method for increasing the yield of catalase by adding a proteinase inhibitor during fermentation process. The proteinase inhibitor is preferably sodium hexametaphosphate. In a preferred embodiment, 1-10 g/L sodium hexametaphosphate is added to the culture medium between 30 to 40 hours of fermentation.

The term "fermentation" refers to large-scale culturing of microorganisms to make products useful for human, including culturing under aerobic and anaerobic conditions.

*Bacillus* sp. WSHDZ-01 strain deposited in China Center for Type Culture Collection (CCTCC) at Wuhan University, Wuhan 430072, People's Republic of China, on Jul. 3, 2007 with accession number CCTCC NO. M206062 is preferably used for production of catalase. The procedure to culture *Bacillus* sp. WSHDZ-01 and produce catalase is described in Chinese patent number ZL200610040898.0, which is incorporated herein by reference.

The advantages of the method of the invention are as follows:
1) The catalase production can be significantly increased by the method of this invention without major changes to original fermentation process;
2) The method of the invention improves the stability of catalase in fermentation broth and reduces loss of enzyme activity during isolation and purification process;
3) This invention utilizes low cost materials and simple operations, which is ideal for industrial application.

Culture Media

The slant culture for preserving *Bacillus* sp. WSHDZ-01 is comprised of 6° Bx malt extract, 1.5%-2.0% agar, pH 7.5.

The liquid seed medium is comprised of 6° Bx malt extract, pH 7.5.

The fermentation medium is comprised of 10 g/L glucose, 5 g/L $NaNO_3$, 0.5 g/L $MgSO_4.7H_2O$, 9.52 g/L $Na_2HPO_4$, 0.6 g/L $KH_2PO_4$, 0.0025 g/L $FeSO_4.7H_2O$, pH 7.0-7.5.

Procedure for Culturing *Bacillus* sp. WSHDZ-01

Slant culture: inoculate *Bacillus* sp. WSHDZ-01 onto the surface of an agar slant culture and incubate it for 10-12 hours at 37° C. Store the slant culture at 4° C. afterwards. Regularly transfer *Bacillus* sp. WSHDZ-01 to a new slant culture to maintain the bacteria strain.

Liquid seed culture: inoculate *Bacillus* sp. WSHDZ-01 grown on the slant culture into 50 ml of liquid seed medium in a 250 ml culture flask. Culture the bacteria at 37° C. for 12-14 hours with a rotation speed at 200 rpm to make a liquid seed culture.

Basic flask culture: Add 6% above liquid seed culture (v/v) to 80 ml basic fermentation culture in a 500 ml culture flask, and incubate at 37° C., 200 rpm for 36-40 hours.

Fermentation Culture: the fermentation process was performed in a 3 liter (L) stirred fermenter (KFT-3L, Korea) with a working volume of 1.8 L. Above 12-h-old basic flask culture was added at a concentration of 5.0% (v/v) to 1.8 L fermentation medium, and incubated under a stepwise temperature control, in which the temperature was maintained at 37° C. for the first 10 hours, at 35° C. during 10-20 hours, and at 32° C. after 20 hours. The aeration rate was 1.0 (v/v/m) (volume of air per volume of culture per minute). The shaking speed was 400 rpm. The total fermentation period was 48 to 53 hours. Proteinase inhibitors can be added during this fermentation process as described below.

Catalase Assay

Catalase activity was measured using the method described by Aebi (Aebi HE. Catalase in vitro. Method Enzymol 1984; 105:121-6). Total reaction volume is 3 ml. 0.1 ml enzyme solution was added to 2.9 ml $KH_2PO_4$—$K_2HPO_4$ buffer (pH 7.0, 10 mM $KH_2PO_4$/50 mM $K_2HPO_4$, 0.45 g/L $H_2O_2$). Decomposition rate of $H_2O_2$ was measured at 240 nm using a UV-Vis spectrophotometer. One unit of catalase activity is defined as the amount of enzyme that decomposes 1 μmol $H_2O_2$ per min at pH 7.0, 25° C.

EXAMPLES

Control culturing procedure was performed in the absence of any protein inhibitors as follows:

*Bacillus* sp. WSHDZ-01 with accession number CCTCC NO. M206062 was used to produce catalase. *Bacillus* sp. WSHDZ-01 grown on a slant culture was inoculated into 50 ml of liquid seed medium in a 250 ml culture flask and cultured at 37° C., 200 rpm for 12-14 hours. 6% above liquid seed culture (v/v) was added to 80 ml basic fermentation culture in a 500 ml culture flask, and incubate at 37° C., 200 rpm, for 36-40 hours.

the fermentation process was performed in a 3 L stirred fermenter (KFT-3L, Korea) with a working volume of 1.8 L. The 12-h-old basic flask culture was added at a concentration of 5.0% (v/v) to 1.8 L fermentation medium, and incubated under a stepwise temperature control, in which the temperature was maintained at 37° C. for the first 10 hours, at 35° C. during 10-20 hours, and at 32° C. after 20 hours. The aeration rate was 1.0 (v/v/m) (volume of air per volume of culture per minute). The shaking speed was 400 rpm. The total fermentation period was 48 to 53 hours.

Extracellular catalase activity measured by the catalase assay described above was 13500±600 U/mL (repeated times n=3).

Example 1

Addition of 3 g/L Hexametaphosphate at 36 Hours of Fermentation

The culturing of *Bacillus* sp. WSHDZ-01 was performed as described under control procedure with one modification, that is, 3 g/L sodium hexametaphosphate was added at 36 hours of fermentation.

Extracellular catalase activity of the fermentation broth measured by the catalase assay described above was 18600 U/mL, a 37.7% increase of enzyme activity from that of the control procedure.

Example 2

Addition of 5 g/L Hexametaphosphate at 36 Hours of Fermentation

The culturing of *Bacillus* sp. WSHDZ-01 was performed as described under control procedure with one modification, that is, 5 g/L sodium hexametaphosphate was added at 36 hours of fermentation.

Extracellular catalase activity of the fermentation broth measured by the catalase assay described above was 19200 U/mL, a 42.2% increase of enzyme activity from that of the control procedure.

Example 3

Addition of 7 g/L Hexametaphosphate at 36 Hours of Ferementation

The culturing of *Bacillus* sp. WSHDZ-01 was performed as described under control procedure with one modification, that is, 7 g/L sodium hexametaphosphate was added at 36 hours of fermentation.

Extracellular catalase activity of the fermentation broth measured by the catalase assay described above was 19700 U/mL, a 45.9% increase of enzyme activity from that of the control procedure.

Example 4

Addition of 1 g/L Hexametaphosphate at 30 Hours of Fermentation

The culturing of *Bacillus* sp. WSHDZ-01 was performed as described under control procedure with one modification, that is, 1 g/L sodium hexametaphosphate was added at 30 hours of fermentation.

Extracellular catalase activity of the fermentation broth measured by the catalase assay described above was 15700 U/mL, a 16.3% increase of enzyme activity from that of the control procedure.

Example 5

Addition of 10 g/L Hexametaphosphate at 40 Hours of Fermentation

The culturing of *Bacillus* sp. WSHDZ-01 was performed as described under control procedure with one modification, that is, 10 g/L sodium hexametaphosphate was added at 40 hours of fermentation.

Extracellular catalase activity of the fermentation broth measured by the catalase assay described above was 16900 U/mL, a 25.2% increase of enzyme activity from that of the control procedure.

Example 6

Hexametaphosphate Increases Storage Stability of Fermentation Broth

The culturing of *Bacillus* sp. WSHDZ-01 was performed as described under control procedure with one modification, that is, 5 g/L sodium hexametaphosphate was added at 36 hours of fermentation.

After fermentation, unpurified fermentation broth was stored at 25° C. for 12 hours. The percentage of remaining extracellular catalase activity of the stored fermentation broth was 56.1% and 84.4% using control culture procedure and the culture procedure with 5 g/L sodium hexametaphosphate, respectively. The broth storage stability was improved by 28.3% under the procedure with sodium hexametaphosphate.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for increasing microbial catalase production, comprising adding 1-10 g/L of the proteinase inhibitor, sodium hexametaphosphate, to the fermentation broth between 30 to 40 hours after the start of a catalase fermentation process using *Bacillus* sp. WSHDZ-01 with the accession number CCTCC No. M206062.

2. The method of claim 1, wherein 7 g/L sodium hexametaphosphate is added between 30 to 40 hours after the start of the catalase fermentation process.

3. The method of claim 2, wherein 7 g/L sodium hexametaphosphate is added at 36 hours after the start of the catalase fermentation process.

4. The method of claim 1, wherein 5 g/L sodium hexametaphosphate is added between 30-40 hours after the start of the catalase fermentation process.

5. The method of claim 1, wherein 3 g/L sodium hexametaphosphate is added between 30-40 hours after the start of the catalase fermentation process.

6. A method to increase the stability of catalase stored in a catalase fermentation broth, comprising adding 1-10 g/L sodium hexametaphosphate to the fermentation broth between 30 to 40 hours after the start of the catalase fermentation process using *Bacillus* sp. WSHDZ-01.

* * * * *